United States Patent [19]

Griffiths et al.

[11] 4,308,109
[45] Dec. 29, 1981

[54] METHOD OF PRODUCING ETHANOL-WATER AZEOTROPE FROM CRUDE ETHANOL

[75] Inventors: Michael J. Griffiths, Haywards Heath, England; Arthur E. Jenkins, Porthcawl, Wales

[73] Assignee: BP Chemicals Limited, London, England

[21] Appl. No.: 193,279

[22] PCT Filed: Oct. 25, 1979

[86] PCT No.: PCT/GB79/00170
§ 371 Date: Jun. 17, 1980
§ 102(e) Date: Jun. 17, 1980

[87] PCT Pub. No.: WO80/00836
PCT Pub. Date: May 1, 1980

[30] Foreign Application Priority Data

Oct. 28, 1978 [GB] United Kingdom ............... 42368/78

[51] Int. Cl.³ .................... B01D 3/40; C07C 29/88
[52] U.S. Cl. ..................................... 203/37; 203/75; 203/76; 203/77; 203/78; 203/79; 203/88; 203/DIG. 13; 203/DIG. 19; 568/921
[58] Field of Search .............. 203/19, 37, 85, 83, 203/76, 79, 78, 92, 93, 99, 95-97, DIG. 19, DIG. 13, 88, 75, 77; 426/494; 568/895, 916, 913, 921; 435/161

[56] References Cited

U.S. PATENT DOCUMENTS 2,551,626  5/1951  Morrell et al. ................... 203/85
2,638,440  5/1953  Drout et al. ..................... 203/85
2,640,017  5/1953  Graff ............................. 203/99
2,806,816  9/1957  Staib et al. ..................... 203/83
2,836,545  5/1958  Catterall et al. ................ 203/93
2,910,412 10/1959  Muller et al. ................... 203/85
3,230,156  1/1966  Katzen .......................... 203/37
3,990,952 11/1976  Katzen .......................... 203/85

FOREIGN PATENT DOCUMENTS 758095  9/1956  United Kingdom ............... 203/76

Primary Examiner—Wilbur L. Bascomb, Jr.
Attorney, Agent, or Firm—Brooks, Haidt, Haffner & Delahunty

[57] ABSTRACT

Process for purifying crude ethanol, whether produced by fermentation or by the synthetic route, to produce a pure ethanol-water azeotrope. The process uses only two distillation columns for fermentation ethanol and only three columns for synthetic ethanol because the latter has diethyl ether as impurity. The inventive concept lies in the design and specification of the columns and the specific distillation conditions which enable each of the impurities in ethanol to be reduced below 1 ppm. Ethanol of such purity is most desirable when used for potable or pharmaceutical purposes. The crude ethanol is fed into a first column and water is separately fed there as well, a side stream of purified aqueous ethanol is withdrawn from the first column and fed to a rectification column where a substantially pure ethanol-water azeotrope is withdrawn as a side stream. The points of introduction and removal of the respective streams to and from the columns are critical for a successful operation and product recovery.

10 Claims, 2 Drawing Figures

METHOD OF PRODUCING ETHANOL-WATER AZEOTROPE FROM CRUDE ETHANOL

The present invention relates to a process for purifying crude ethanol to produce a substantially pure ethanol-water azeotrope which may be dried subsequently.

In conventional processes, the crude ethanol whether produced by fermentation, of molasses or grain by yeast, or by the synthetic route eg by the hydration of ethylene, is in the form of a dilute aqueous solution and has always been subjected to a series of distillation and absorption stripping operations, to obtain an ethanol-water azeotrope essentially free from all impurities. These operations were designed to remove impurities such as, for instance, acetaldehyde, diethyl ether, and butanols. Depending upon the process by which the crude ethanol is made at least four columns and usually six or more columns have been used to obtain in ethanol-water azeotrope from which substantially all impurities have been removed.

To obtain this high purity product, the crude ethanol stream is normally first subjected to hydroselective distillation in one or more towers. The term hydroselective distillation is used to refer to a hydroextractive process in which the impurities and the desired product components are separated in such a manner that neither the impurities nor the desired product components leave the column with the extractant. Very considerable dilution of the crude ethanol by water produces an inversion of volatilities, so that the impurities such as higher alcohols, eg butanols, can be removed overhead in the hydroselective distillation. The relatively lower boiling impurities, such as acetaldehyde and ether normally remain more volatile and are also removed overhead. Aqueous ethanol stripped of impurities is removed as a sidestream fraction from the lower part of the hydroselective distillation column, and is then concentrated or rectified, typically in the presence of alkali, in the next column, normally known as the rectifier, to produce ethanol-water azeotrope as a sidestream fraction free of higher boiling impurities such as butanols, from the upper part of the column. As a rule a small lower sidestream of butanols, which have escaped removal in the hydroselective distillation, is also removed from the rectifier and is further processed in an additional column termed the butanol column to recover ethanol for recycle. The base product from the rectifier consists of relatively pure but dilute aqueous ethanol and this is normally fed to a stripper column, which recovers the ethanol as an overhead fraction for recycle to the rectifier. An additional column may also be required to remove water and ethanol from the impurities stream obtained as an overhead fraction from the hydroselective distillation, prior to disposing of the impurities eg by burning in a thermal oxidiser. The number of separate distillation columns required to achieve these functions in the accepted contemporary processes represents not only an enormous capital investment in terms of the plant but also decreases the economic efficiency of the process in terms of energy inputs, maintenance costs and incomplete recovery of products. Some expedients have been suggested to reduce the actual number of columns but these expedients have involved fewer columns which are nevertheless much larger to make up for the volume and capacity of the columns omitted. Consequently there is no appreciable saving either in capital costs or energy inputs. It has now been found that by operating the distillations under specific conditions the process can be reduced to no more than three columns, and in some cases two columns, with actual reduction in total column capacity, energy inputs, maintenance and capital costs.

Accordingly the present invention is a process for purifying crude ethanol to obtain substantially pure ethanol-water azeotrope, comprising separately feeding the crude ethanol and water into a single hydroselection column having a refluxing section above the water feed point, an intermediate section between the water feed point and the crude ethanol feed point, a stripping section between the crude ethanol feed point and the product side draw tray, and a base section below the product side draw tray wherein the ratio of theoretical trays in the refluxing, intermediate and stripping sections is in the range 1:3.4–5.5:8–11, the hydroselection column containing at least 66 actual trays and being operated at temperatures between 250° F. and 350° F. and at a pressure above 50 psia, the water being fed to the column at a point above the crude ethanol feed point and the molar ratio of water fed to ethanol in the crude ethanol feed being at least 10:1, withdrawing an overhead vapour fraction containing substantially all of the volatile impurities, and returning part of the overhead vapour fraction after condensation to the column as liquid reflux maintaining a reflux ratio of at least 200:1 expressed on the distillate product, withdrawing a purified aqueous ethanol sidestream substantially free from all impurities from the product side draw tray below the crude ethanol feed point, feeding the purified aqueous ethanol into the lower half and optionally aqueous alkali into the upper half of a rectification column, said column being operated at temperatures between 160° and 250° F., recycling an overhead purge stream containing acetaldehyde and other impurities to the crude ethanol feed to the hydroselection column, and withdrawing a substantially pure ethanol-water azeotrope containing less than 5 ppm of any of the impurities, except methanol, in the crude ethanol feed as a sidestream from a point above the aqueous alkali feed, if any, to the column and an alkaline aqueous effluent substantially free from ethanol from the base of the column.

According to a further embodiment, the present invention is a process for purifying crude ethanol, produced by catalytic hydration of ethylene, to obtain substantially pure ethanol-water azeotrope comprising feeding crude ethanol into the top half of an ether flash column operated to take off overhead a fraction containing a major proportion of diethyl ether and from the base of the column an aqueous ethanol stream substantially reduced in diethyl ether content with respect to the starting material, separately feeding the latter aqueous ethanol stream and water into a single hydroselection column having a refluxing section above the water feed point, an intermediate section between the water feed point and the aqueous ethanol feed point, and a stripping section between the aqueous ethanol feed point and the product side draw tray, and a base section below the product side draw tray wherein the ratio of theoretical trays in the refluxing, intermediate and stripping sections is in the range 1:3.4–5.5:8–11 the hydroselection column containing at least 66 trays and being operated at temperatures between 250° F. and 350° F. and at a pressure above 50 psia, the water being fed to the column at a point above the aqueous ethanol feed point and the molar ratio of water fed to ethanol in the aqueous ethanol feed being at least 10:1, withdrawing an overhead vapour fraction containing substantially all of the volatile impurities, and returning part of the overhead fraction after condensation to the column as liquid reflux maintaining a reflux ratio of at least 200:1 expressed on the distillate product, withdrawing a purified aqueous ethanol sidestream substantially free from all impurities from the product side draw tray below the aqueous ethanol feed point, feeding the purified aqueous ethanol into the lower half and aqueous alkali into the upper half of a rectification column, said column being operated at temperatures between 160° and 250° F., recycling an overhead purge stream containing acetaldehyde and other impurities to the aqueous ethanol feed to the hydroselection column, and withdrawing a substantially pure ethanol-water azeotrope containing less than 5 ppm of any of the impurities in the crude ethanol starting material as a sidestream from a point above the aqueous alkali feed to the column and an alkaline aqueous effluent substantially free from ethanol from the base of the column.

The crude ethanol fed to the hydroselection column suitably contains between 5 and 20% by weight of ethanol, preferably between 10 and 15% by weight of ethanol. The molar ratio of water fed to the ethanol in the crude ethanol feed is at least 10:1, and preferably from 11 to 13:1. The feeds to the hydroselection column are suitably fed at or below their respective bubble points at the appropriate feed tray pressure. The hydroselection column has at least 66 actual trays and preferably between 70 and 90 actual trays.

The temperature profile within the hydroselection column is chosen to maximise the relative difference in volatilities between impurities and ethanol. It is preferably between 260° and 320° F. The pressure in the hydroselection column is suitably between 70 and 100 psia, preferably between 75 and 85 psia.

Operating under these conditions, an overhead vapour fraction containing substantially all of the volatile impurities is withdrawn from the column. The bulk of these overhead vapours are refluxed after condensation and returned to the top tray of the column suitably maintaining a reflux ratio of at least 260:1, preferably in the range of 260 to 280:1 expressed on distillate product. In this reflux system the liquid reflux is normally a single phase liquid, but if two phases are present these should be adequately mixed before being returned as reflux to the top of the column. The remainder of the overhead vapour fraction containing the bulk of the volatile impurities contained in the feed is disposed of eg by feeding to a conventional thermal oxidiser.

The purified aqueous ethanol withdrawn as a sidestream from the hydroselection column is substantially free from all impurities, particularly the butanols, which thus eliminates the need for a further column for the removal of butanols. The sidestream containing the purified aqueous ethanol is fed into the lower half of the rectification column, and optionally aqueous alkali is fed into the top half of this column. Aqueous alkali may not be necessary for purifying certain varieties of fermentation ethanol which do not produce acetaldehyde as an impurity. The feed rate of the aqueous alkali, where used, is suitably in the range 5 to 8 liters, preferably 5 to 6 liters, of 20% w/w aqueous caustic soda per 1000 liters of ethanol azeotrope product. The rectification column preferably has between 65 and 75 trays. This column is preferably operated at a temperature between 170° F. and 240° F. The head pressure in this column may vary, eg between atmospheric and 25 psia. Under these conditions the rectifier is confined to separating ethanol from the bulk of the water and a substantially pure azeotrope stream containing between 85 and 89 mole % of ethanol is recovered as a sidestream from a point above the aqueous alkali feed, if any, to the column. This ethanol-water azeotrope contains less than 5 ppm of any of the impurities, except methanol, in the starting material and under optimum conditions it is possible to reduce this level below 1 ppm of each impurity. The exception with regard to methanol impurity only arises in the case where the crude ethanol is produced by a fermentation process. Reflux to the rectification column is provided in the usual way by recycling condensed overhead vapours. A small overhead purge stream from this column is recycled back to the hydroselection column by mixing it with the crude ethanol feed to that column. Optionally, a small sidestream from the lower half of the rectification column may also be recycled to the crude ethanol feed to the hydroselection column further to improve the quality of the ethanol-water azeotrope product. Another feature of the present invention is that the alkaline aqueous effluent removed from the base of the rectification column is substantially free from ethanol.

The above procedure of obtaining substantially pure ethanol-water azeotrope may be used for crude ethanol whether produced by the synthetic or the fermentation route. In some cases, the crude ethanol produced by the synthetic route contains significant amounts of diethyl ether as impurity. In such cases, the procedure may be modified to include a small ether flash column in the process whereby a major proportion of the diethyl ether content of the crude ethanol stream is removed prior to its being fed into the hydroselection column.

The ether flash column into which the crude synthetic ethanol is fed suitably contains between 10 and 20 actual trays. This column is suitably operated at a temperature of between 150° and 230° F. and a pressure between 15 and 25 psia. The reflux ratio in this column is preferably between 90:1 and 100:1, typically 95:1.

The crude synthetic ethanol fed into the top half of the column suitably has a concentration of between 5 and 20% by weight. This column is suitably operated with a reflux stream of condensed overheads which is predominantly ether, accompanied by small quantities of acetaldehyde and ethanol. The column is preferably operated with a sufficiently high reflux ratio to ensure that the overhead product stream is low in acetaldehyde and ethanol concentration. The overheads from this column may either be returned to the reactor in which ethanol synthesis is carried out or may be fed to a thermal oxidiser for burning. The loss of any ethanol by adopting the latter procedure is insignificant since it is unlikely to be more than 5% by weight of the ether recovered overhead.

An aqueous ethanol stream having a substantially reduced ether content but otherwise of practically the same concentration as the crude synthetic ethanol feed to the ether flash column is then withdrawn from the base of this column and fed to the hydroselection column. The rest of the procedure is the same as before.

The invention is further illustrated in the accompanying flow diagrams in which

Figure 1:
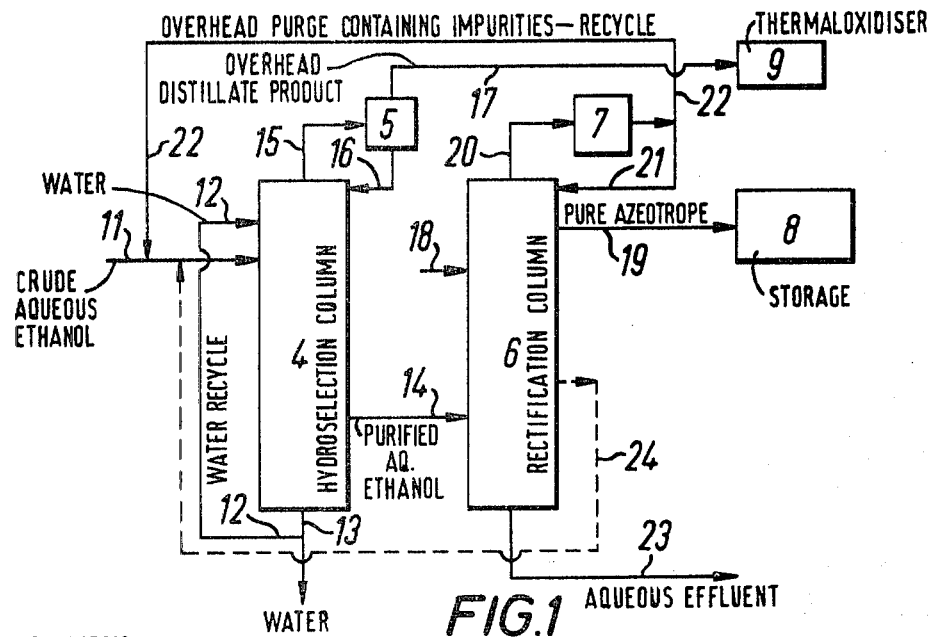
FIG. 1 represents the embodiment without the ether flash column.
Figure 2:
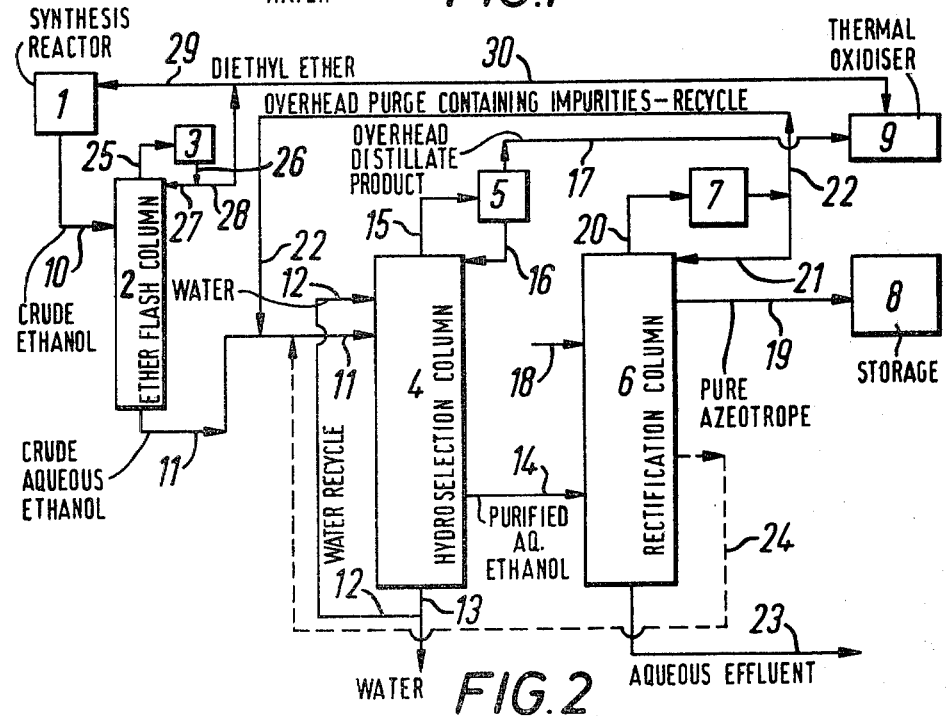
FIG. 2 represents the embodiment with the ether flash column.

The process shown by FIG. 2 also embraces the process features covered by FIG. 1 and the following description applies where appropriate to both FIG. 1 and FIG. 2.

Referring first to FIG. 2, the crude synthetic ethanol is produced by the catalytic hydration of olefins in reactor 1. The crude ethanol is a dilute aqueous solution of approximately 12% w/w concentration and contains diethyl ether, aldehydes and butanols as impurities.

The crude ethanol is fed via line 10 into the top half of an ether column 2 from which an overhead fraction containing a major proportion of diethyl ether is removed by line 25, condensed in condenser 3 and is then partially recycled via line 26 and 27 as reflux to the top of column 2 the remainder being withdrawn as a purge stream via line 28. This purge stream may be either recycled back to the synthesis reactor 1 via line 29 or disposed of via line 30 to a thermal oxidiser 9 for burning. An aqueous ethanol stream substantially reduced in diethyl ether content is withdrawn from the base of column 2 and is fed into the top half of a hydroselection column 4 via line 11. In the process shown in FIG. 1, which does not have an ether flash column, the crude ethanol is fed directly into the top half of the hydroselection column 4 via line 11. In the hydroselection column 4 the ratio of theoretical trays in the refluxing, intermediate and stripping sections is in the range 1:3—4–5.5:8–11 and the column contains at least 66 actual trays. Water is also fed into column 4 via line 12. The molar ratio of water fed via line 12 to the ethanol content of the feed via line 11 is at least 10 to 1. By operating at these dilutions the volatilities of the major impurities are inverted relative to ethanol and substantially all the butanols, a major portion of the aldehydes and any remaining diethyl ether are removed as overheads via line 15. Column 4 is operated with a liquid reflux via line 16 which is formed by feeding the overheads via line 15 into a condenser and reboiler cum condenser 5 and an impurities purge stream containing butanols, ethers, and aldehydes is withdrawn via line 17 for the purpose of burning in the thermal oxidiser 9. An aqueous stream 13 is withdrawn from the base of column 4, a part of which is recycled via line 12 as the water feed to the column. The remainder maybe disposed of as effluent. A purified aqueous ethanol side stream substantially free from butanols is withdrawn from column 4 via line 14 and fed to the lower half of a rectification column 6. Caustic alkali is also fed to column 6 via line 18. An overhead purge stream containing acetaldehyde and other impurities is withdrawn from this column via line 20 part of this stream being returned as reflux via line 21 through a condenser 7, the remainder being returned to the crude ethanol feed line 11 via line 22. Substantially pure ethanol-water azeotrope containing only a marginal excess of water and less than 5 ppm of impurities is withdrawn via line 19 for storage at 8. This can be dried as and when necessary by known methods. A bottoms fraction consisting of alkaline water containing substantially no ethanol is withdrawn from the base of column 6 via line 23 and discharged as effluent. If necessary a purge stream can be withdrawn from column 6 via line 24 and recycled to the crude ethanol feed line 11.

It will be understood by those skilled in the art that the references to trays in the various columns are meant to include equivalent heights of column packing to achieve a similar split of of the products.

The invention is further illustrated with reference to the following Example.

EXAMPLE.

A stream of crude synthetic aqueous ethanol (containing by weight 12.45% ethanol, 0.16% diethylether, 0.023% secondary and tertiary butanols, and 0.035% acetaldehyde) produced by catalytic hydration of ethylene was fed as a liquid into a 14-tray ether flash column on the 9th tray from the bottom. This column was operated at a head temperature of 157° F., a head pressure of 18 p.s.i.a. and a reflux ratio of 95:1. The diethyl ether in the feed to the column was withdrawn overhead and recycled to the synthesis reactor. From the base of this column, an aqueous ethanol stream (containing by weight 12.46% ethanol, 0.015% diethyl ether, 0.023% butanols and 0.023% aldehydes) was fed into an 80-tray hydroselection column on the 58th tray. A calculated amount of water was also fed into the hydroselection column on the 76th tray to maintain a molar ratio of water fed to the ethanol content in the feed to the column at about 11.5:1. The hydroselection column was operated with a temperature profile of between 265° F. (at the top) and 318° F. (at the base) and a head pressure of 80 p.s.i.a., with a reflux above the water feed point. From the column an overhead vapour fraction containing substantially all of the volatile impurities was withdrawn and part of this fraction was condensed and returned to the column as reflux to maintain a reflux ratio of 268:1 expressed on the distillate product. The rest of the fraction was fed into a thermal oxidiser to be burnt. A purified aqueous ethanol stream (containing as impurities less than 1 ppm secondary butanol, less than 1 ppm tertiary butanol, less than 1 ppm acetaldehyde and 24 ppm diethyl ether) was withdrawn as vapour from the column between product side draw trays 18 and 19. The base product from this column was mainly water which could be discarded as effluent or optionally recycled to the water feed to the column. The purified aqueous ethanol withdrawn from the product side draw tray was fed into a 70 tray rectifying column on the 16th tray. An aqueous solution of caustic alkali (concentration 20% by weight) was introduced into the column on the 51st tray. This column was operated with a temperature profile of between 173° F. (at the top) and 234° F. (at the base), and a head pressure of 15 p.s.i.a. A small overhead purge stream containing acetaldehyde and other impurities was recycled to the aqueous ethanol feed to the hydroselection column. A substantially pure ethanol-water azeotrope (containing between 86 and 87% by weight of ethanol and less than 1 ppm of each of the impurites) was withdrawn as a side stream from the 63rd tray of this column. The base product from this column was an aqueous alkaline effluent which contained only traces of ethanol (2 ppm).

We claim:

1. A process for purifying crude ethanol to obtain substantially pure ethanol-water azeotrope, comprising separately feeding the crude ethanol and water into a single hydroselection distillation column having a refluxing section above the water feed point, an intermediate section between the water feed point and the crude ethanol feed point, a stripping section between the crude ethanol feed point and a product side draw tray below the crude ethanol feed point, and a base section between the product side draw tray wherein the ratio of theoretical trays in the refluxing, intermediate and stripping sections is in the range 1:3.4–5.5:8–11, the hydroselection distillation column containing at least 66 actual trays and being operated at temperatures between 250° F. and 350° F. and at a pressure above 50 psia, the water being fed to the column at a point above the crude ethanol feed point and the molar ratio of water fed to ethanol in the crude ethanol feed being at least 10:1, withdrawing an overhead vapour fraction containing a substantial portion of volatile impurities, and returning part of the overhead vapour fraction after condensation to the column as liquid reflux maintaining a reflux ratio of at least 200:1 expressed on the distillate product, withdrawing a purified aqueous ethanol sidestream substantially free from all impurities from the product side draw tray below the crude ethanol feed point, feeding the purified aqueous ethanol into the lower half of a rectification column, said column being operated at temperatures between 160° and 250° F., recycling an overhead purge stream containing acetaldehyde and other impurities from the rectification column to the crude ethanol feed to the hydroselection column, and withdrawing a substantially pure ethanol-water azeotrope containing less than 5 ppm of any of the impurities, except methanol, in the crude ethanol feed as a sidestream from the upper half of the column and an aqueous effluent substantially free from ethanol from the base of the column.

2. A process for purifying crude ethanol, produced by catalytic hydration of ethylene, to obtain substantially pure ethanol-water azeotrope comprising feeding crude ethanol into the top half of an ether flash column operated to take off overhead a fraction containing a major proportion of diethyl ether and from the base of the column an aqueous ethanol stream substantially reduced in diethyl ether content with respect to the starting material, separately feeding the latter aqueous ethanol stream and water into a single hydroselection distillation column having a refluxing section above the water feed point, an intermediate section between the water feed point and the aqueous ethanol feed point, and a stripping section between the aqueous ethanol feed point, and a product side draw tray below the aqueous ethanol feed point, and a base section below the product side draw tray wherein the ratio of theoretical trays in the refluxing, intermediate and stripping sections is in the range 1:3.4–5.5:8–11 the hydroselection distillation column containing at least 66 actual trays and being operated at temperatures between 250° F. and 350° F. and at a pressure above 50 psia, the water being fed to the column at a point above the aqueous ethanol feed point and the molar ratio of water fed to ethanol in the aqueous ethanol feed being at least 10:1, withdrawing an overhead vapour fraction containing a substantial portion of volatile impurities, and returning part of the overhead fraction after condensation to the column as liquid reflux maintaining a reflux ratio of at least 200:1 expressed on the distillate product, withdrawing a purified aqueous ethanol sidestream substantially free from all impurities from the product side draw tray below the aqueous ethanol feed point, feeding the purified aqueous ethanol into the lower half and aqueous alkali into the upper half of a rectification column, said column being operated at temperatures between 160° and 250° F., recycling an overhead purge stream containing acetaldehyde and other impurities from the rectification column to the aqueous ethanol feed to the hydroselection distillation column, and withdrawing a substantially pure ethanol-water azeotrope containing less than 5 ppm of any of the impurities in the crude ethanol starting material as a sidestream from a point above the aqueous alkali feed to the column and an alkaline aqueous effluent substantially free from ethanol from the base of the column.

3. A process according to claim 1 or 2 wherein the crude ethanol fed to the hydroselection column contains between 5 and 20% by weight of ethanol.

4. A process according to claims 1 or 2 wherein the molar ratio of water fed to the ethanol in the crude ethanol feed is from 11 to 13:1.

5. A process according to claims 1 or 2 wherein the feeds to the hydroselection column are fed at or below their respective bubble points at the appropriate feed tray pressure.

6. A process according to claims 1 or 2 wherein the hydroselection column has between 70 and 90 actual trays.

7. A process according to claims 1 or 2 wherein the head pressure in the hydroselection column is between 70 and 100 psia.

8. A process according to claims 1 or 2 wherein the rectification column is operated at a head temperature between 170° F. and 240° F. and a head pressure between atmospheric and 25 psia.

9. A process according to claim 2 wherein the ether flash column into which the crude ethanol is fed contains between 10 and 20 trays and is operated at a head temperature of between 150° and 250° F. and a head pressure between 15 and 25 psia.

10. A process according to claim 2 wherein the aqueous alkali feed rate to the rectification column is in the range 5 to 8 liters of 20% w/w aqueous caustic soda per 1000 liters of ethanol azeotrope product.

* * * * *